United States Patent
Gilad (10) Patent No.: US 7,678,043 B2
(45) Date of Patent: Mar. 16, 2010

(54) DEVICE, SYSTEM AND METHOD FOR IN-VIVO SENSING OF A BODY LUMEN

(75) Inventor: Zvika Gilad, Haifa (IL)

(73) Assignee: Given Imaging, Ltd., Yoqneam (IL)

( * ) Notice: Subject to any disclaimer, the term of this patent is extended or adjusted under 35 U.S.C. 154(b) by 1045 days.

(21) Appl. No.: 11/319,772

(22) Filed: Dec. 29, 2005

(65) Prior Publication Data
US 2007/0156015 A1 Jul. 5, 2007

(51) Int. Cl.
*A61B 1/00* (2006.01)

(52) U.S. Cl. .................. 600/109; 600/160; 600/141

(58) Field of Classification Search ............ 600/101, 600/160, 109, 128, 141
See application file for complete search history.

(56) References Cited

U.S. PATENT DOCUMENTS

| | | | | |
|---|---|---|---|---|
| 3,042,030 | A * | 7/1962 | Read | 128/831 |
| 4,278,077 | A | 7/1981 | Mizumoto | |
| 4,626,213 | A * | 12/1986 | Shiner et al. | 433/173 |
| 5,604,531 | A | 2/1997 | Iddan et al. | |
| 5,662,587 | A * | 9/1997 | Grundfest et al. | 600/114 |
| 5,993,212 | A * | 11/1999 | Shiner | 433/172 |
| 5,993,378 | A | 11/1999 | Lemelson | |
| 6,240,312 | B1 | 5/2001 | Alfano et al. | |
| 6,350,076 | B1 * | 2/2002 | Wagner et al. | 403/135 |
| 6,936,003 | B2 | 8/2005 | Iddan | |
| 6,951,536 | B2 * | 10/2005 | Yokoi et al. | 600/128 |
| 7,192,397 | B2 * | 3/2007 | Lewkowicz et al. | 600/160 |
| 7,442,166 | B2 * | 10/2008 | Huang et al. | 600/160 |
| 2001/0035902 | A1 | 11/2001 | Iddan et al. | |
| 2002/0103417 | A1 | 8/2002 | Gazdzinski | |
| 2002/0173718 | A1 | 11/2002 | Frisch | |
| 2003/0018280 | A1 * | 1/2003 | Lewkowicz et al. | 600/549 |
| 2004/0199054 | A1 * | 10/2004 | Wakefield | 600/160 |
| 2006/0149386 | A1 * | 7/2006 | Clarke et al. | 623/18.12 |
| 2007/0043263 | A1 * | 2/2007 | Wakefield | 600/160 |
| 2007/0099469 | A1 * | 5/2007 | Sorensen | 439/289 |
| 2007/0173691 | A1 * | 7/2007 | Yokoi et al. | 600/118 |
| 2007/0173696 | A1 * | 7/2007 | Fujimori et al. | 600/158 |
| 2008/0114204 | A1 * | 5/2008 | Fujimori et al. | 600/130 |

FOREIGN PATENT DOCUMENTS

| | | |
|---|---|---|
| DE | 344 0177 | 5/1986 |
| JP | 57-45833 | 3/1982 |
| JP | 4-109927 | 4/1992 |
| JP | 1992-144533 | 5/1992 |
| JP | 2007-181682 | 7/2007 |
| SU | 1768945 A1 * | 10/1992 |
| WO | WO 2004-058041 | 7/2004 |
| WO | WO 2005-112460 | 11/2005 |

OTHER PUBLICATIONS

U.S. Appl. No. 10/879,053, filed Jun. 30, 2004, Horn.

* cited by examiner

*Primary Examiner*—John P Leubecker
(74) *Attorney, Agent, or Firm*—Pearl Cohen Zedek Latzer, LLP (57) ABSTRACT

A system device and a method for imaging and/or for obtaining a sample from, for example, endo-luminal areas. The system may include two or more devices which may be magnetically connected in a body lumen, for example the system may include a first device which may include an imager and a transmitter for transmitting in vivo data, and a second device which may include a sampling mechanism.

20 Claims, 8 Drawing Sheets

DEVICE, SYSTEM AND METHOD FOR IN-VIVO SENSING OF A BODY LUMEN

FIELD OF THE INVENTION

The present invention relates generally to the field of sensing and/or biopsies of endo-luminal areas, and to such methods using two or more in-vivo devices.

BACKGROUND OF THE INVENTION

Known devices may be helpful in providing in-vivo sensing, such as imaging or pH sensing. Autonomous in-vivo sensing devices, such as swallowable or ingestible capsules or other devices may move through a body lumen, sensing as they move along. An autonomous in-vivo sensing device such as an imaging device may include, for example, an imager for obtaining images from inside a body cavity or lumen, such as the gastrointestinal (GI) tract. The imager may, for example, be associated with an optical system, and optionally a transmitter and an antenna. Some of these devices use a wireless connection to transmit image data.

SUMMARY OF THE INVENTION

In one embodiment of the invention, there is provided a system for imaging for example a body lumen (e.g., the gastrointestinal tract) and/or obtaining a sample from within a body lumen. According to one embodiment the system may include a plurality of devices which may be for example inserted separately, e.g. one by one, into a body lumen, for example by swallowing, and may be later be joined in a body lumen using for example a connection unit. That the plurality of devices may be swallowed separately may make swallowing the system easier than swallowing a plurality of connected devices.

According to some embodiments of the present invention, the system may include a first device which may include an imager and a transmitter for transmitting in vivo data (e.g., image data), and another device which may include a sampling mechanism.

According to some embodiments devices and/or systems according to embodiments of the invention may be swallowable or otherwise inserted into a patient's gastrointestinal tract.

According to a further embodiment of the invention there is provided a method for imaging body lumens, such as the large intestine or the stomach and/or for obtaining a sample from within a body lumen. The method according to one embodiment of the invention may include the step of inserting two or more in-vivo devices into a patent lumen, for example by swallowing the devices. In an embodiment of the invention the method may be used for transmitting images of the body lumen and/or controlling the sampling mechanism, e.g., to obtain a biopsy sample from within the body lumen.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be appreciated by one skilled in the art that the present invention may be practiced without the specific details presented herein. Furthermore, well known features may be omitted or simplified in order not to obscure the present invention.

Figure 1A:
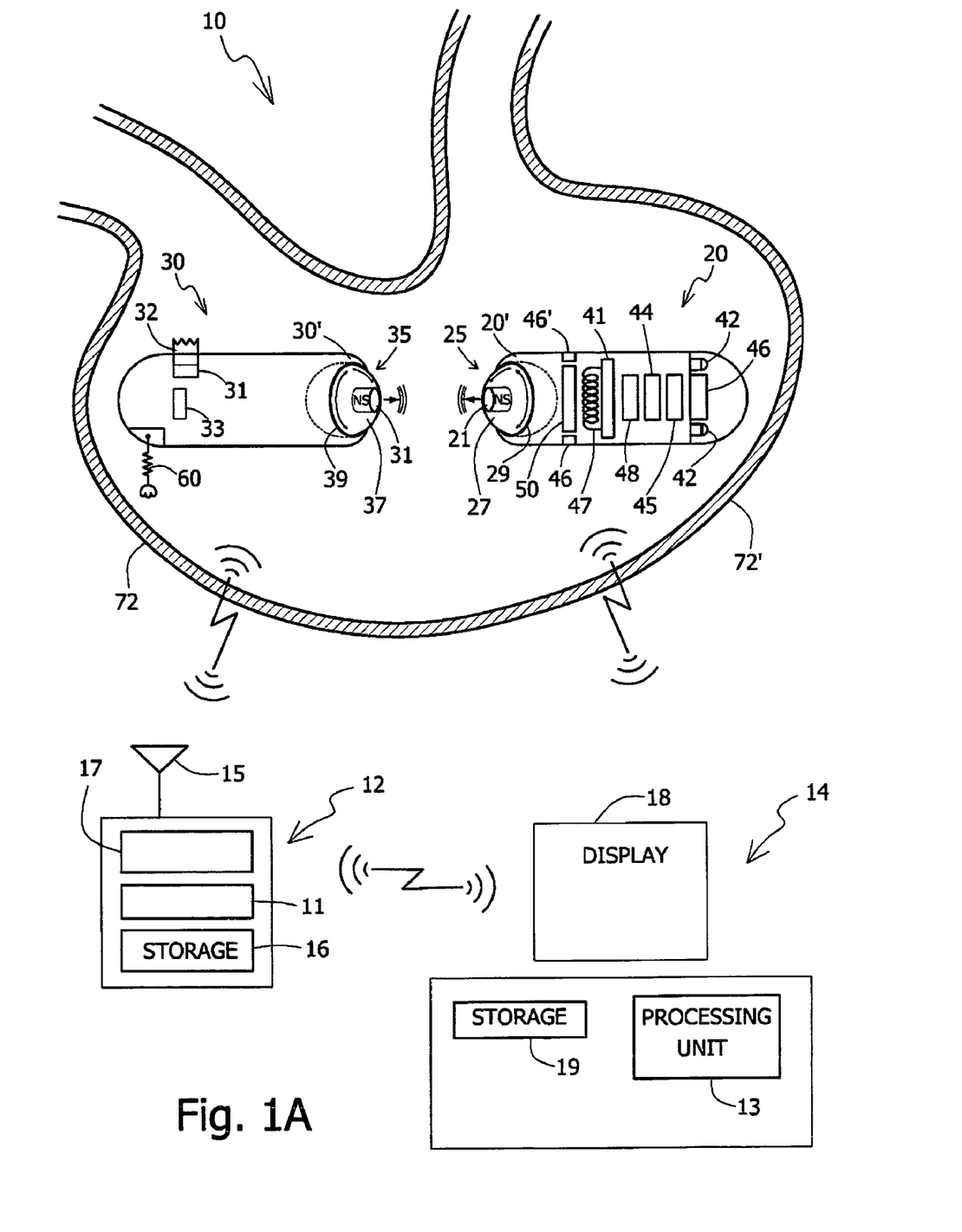
FIG. 1A is a schematic illustration of an embodiment of an in-vivo system and an external receiver and transmitter system in accordance with an embodiment of the invention.
Figure 1B:
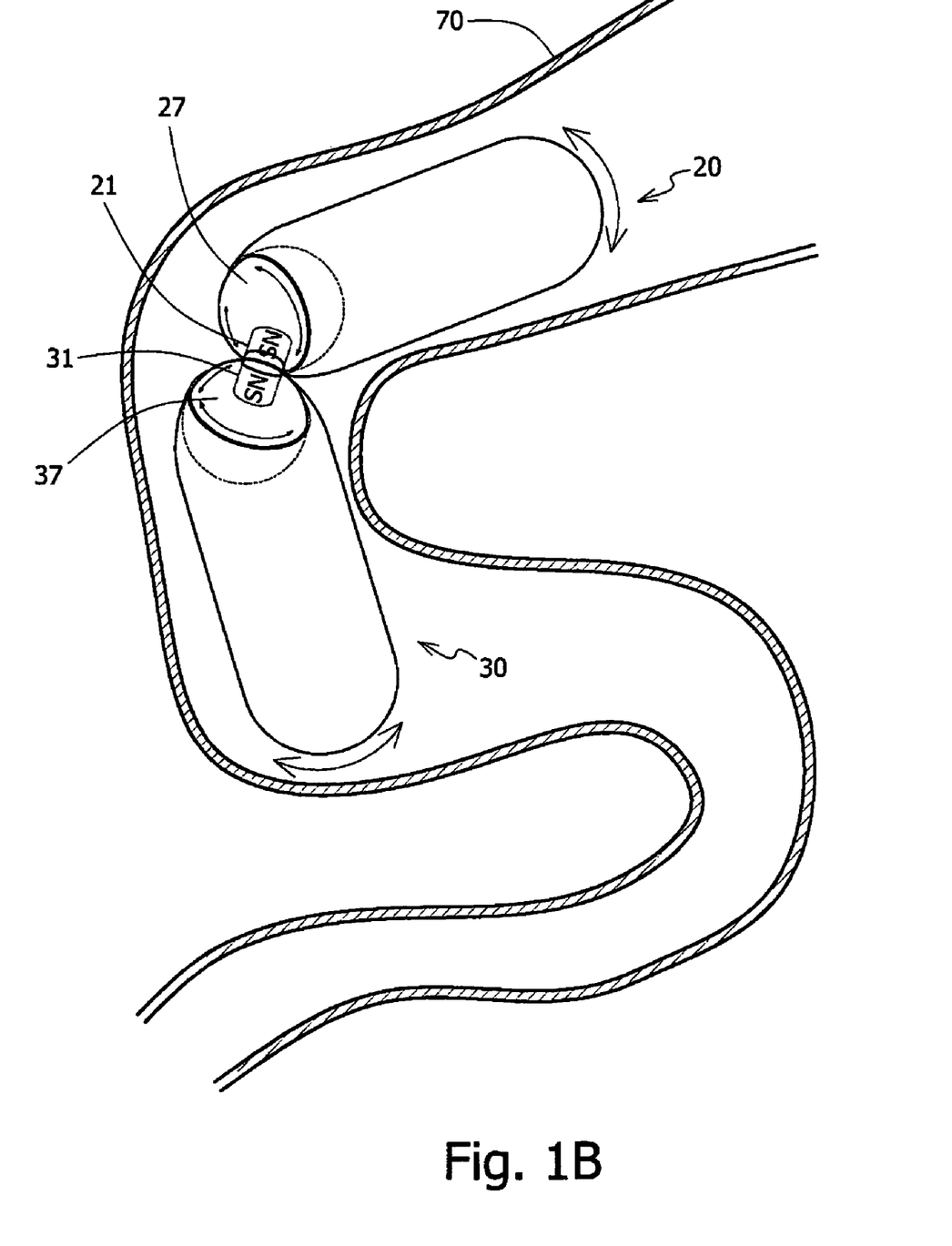
FIG. 1B is a schematic illustration of an in-vivo system in accordance with an embodiment of the present invention.

Reference is made to FIGS. 1A-1B, which schematically illustrate a number of in-vivo devices, which may be magnetically connected, in accordance with an embodiment of the present invention. System 10 may include one or more devices, such as a first device e.g. an autonomous in-vivo device 20, a second device e.g. an autonomous in-vivo device 30, an external receiving device and/or recording device 12, e.g. data receiver, and a workstation 14. While two devices connected or chained together are shown, other numbers of devices may be connected or chained. Devices of system 10, e.g. devices 20 and 30, may be introduced separately into an endo-luminal cavity 72 such as for example by swallowing, and may be later be joined to one another, as shown in FIG. 1B in a body lumen e.g. the stomach 70. The plurality of devices may be autonomously engaged in a body lumen e.g. may move from a separated configuration to a connected configuration by themselves by, for example, one or more magnets, such as a "connecting magnet". The term "connecting magnet" in the present invention may refer to a magnet positioned inside a device, such that one side of the magnet is facing the internal part of a device and the other side of the magnet is facing outward, e.g. towards a body lumen, thus enabling the engagement of a device, such as an in-vivo imaging device 20, to another device, such as device 30.

According to one embodiment of the present invention device 20 may include a connecting magnet 21 placed for example at the edge 20' of device 20, while device 30 may include a matching connecting magnet 31 placed for example, at the edge 30' of device 30. The connecting magnets 21 and 31 may be attached, or may be part of connection unit(s) such as a ball-and-socket joint connection units 25 and 35. The ball-and-socket joint connection units 25 and 35, may include joint balls 27 and 37 and joint sockets 29 and 39 e.g. spherical well for receiving the joint balls 27 and 29. For example, as shown in FIG. 1A, when the devices 20 and 30 are still separated from one another but are located in close proximity from one another, for example in the stomach, a magnetic field is created by the two connecting magnets 21 and 31 such that the two devices 20 and 30 are drawn to one another. After the two devices 20 and 30 are connected, the joint balls 25 and 35 and the devices 25 and 35 may rotate in several axes.

According to some embodiments of the present invention, the ball-and-socket connection between the two devices such as devices 20 and 30 of system 10 may enable a more pliable and maneuverable movement of the devices 20 and 30, for example in an endo-luminal cavity 72, than would be a single rigid or partially flexible system of the same size or mass.

In some embodiments one device, link or lobe of system 10 may include for example a device 20 which may include one or more imagers such as imagers 46 and 46', for capturing image frames or a stream of image frames, an illumination source 42, for illuminating the body lumen, a power source 45 for powering device 20 and/or device 30, a processor 44 for processing data and commands to and from device 20 and/or device 30, and a transmitter 41 with an antenna 47, for transmitting image and possibly other data to an external receiver 12 or to other devices such as device 30.

According to some embodiments another device or lobe 30 of system 10 may include a power source 33, such as a battery, and a biopsy or sampling mechanism 32 which may include a storage chamber 31.

In some embodiments of the present invention, in-vivo device 20 may include one or more sensors 48, in addition to imagers 46 and 46', for example, temperature sensors, pH sensors, pressure sensors, blood sensors, tracking sensors, etc. Imagers 46 and 46' may be a CCD or CMOS imager, or may be another solid state imaging device or other imaging device. Illumination source 42 may include one or more LEDs (Light Emitting Diode), OLEDs (Organic LED) or other illumination sources.

One device may capture and transmit images of another device; for example of a sampling chamber of another device. For example, images of samples may be transmitted, or images of samples reacting with a substance. In some embodiments, a first device such as device 20 that may contain an imager 46 may capture an image of some portion or all, of the other device e.g. a second device 30, and perhaps a portion of the GI tract surrounding the device 30. A device that may have an imager 46 at a front and back portion of such device 20 may capture an image of an endo-luminal area with, for example, a front imager 46 and an image of the other connected device with a back imager 46'. In some embodiments an imager is included in both devices 20 and 30 and the imagers may view an area in front of the devices 20 and 30. According to some embodiments, one imager may be turned off while another imager may be turned on, or both or neither of the imagers may be turned on at the same time.

Similarly, one imager may view an area behind the devices 20 and 30, and another may view an area in front of the devices 20 and 30.

According to an embodiment of the invention either one or both devices 20 and 30 may be swallowed, or otherwise inserted within a gastrointestinal (GI) tract and may pass through the GI tract, for example, via natural peristaltic motion while capturing a series of image frames, e.g. capturing image frames periodically at for example two frames per second. In other embodiments of the present invention, the in-vivo imaging devices, such as device 20, may advance through the GI tract via other suitable means and may capture image frames at other suitable rates, for example, at variable rates. Image frames captured as well as other data may be transmitted externally for processing and display. According to one embodiment of the present invention, tracking data, tracking the location of the in-vivo imaging device over time or over the course through the GI tract may be included in the processing and display of data. Data captured may be processed to automatically select image frames that may be candidates for content diagnosis.

The in-vivo device 20 may transmit information (e.g., images or other data) to an external receiver 12 possibly close to or worn on a subject. Typically, the receiver 12 may include an antenna or antenna array 15 and a data receiver storage unit 16. Antenna array 15 may pick up signals transmitted by device 20 or the transmitter 41 and antenna 47 of device 20. The external receiver 12 may include one or more processors 17 for processing image data or other data. Receiver 12 may include a tracking unit 11, for tracking the location of an autonomous in-vivo device, such as device 20 and/or device 30, over time. For example, tracking unit 11 may track the location of device 20 in three dimensional space over time and/or may track the distance, for example the distance over time that device 20 and/or device 30 traveled through the GI tract or through a specific organ in the GI tract over time. Such tracking may be similar to various embodiments described, for example, in U.S. Patent Application Publication No. US-2002-0173718-A1 published on Nov. 21, 2002 and U.S. patent application Ser. No. 10/879,053 filed on Jun. 30, 2004 both of which are assigned to the common assignee of the present application and incorporated herein by reference in their entirety. Other known tracking units or methods of tracking a device may be used. In other embodiments, the tracking unit 11 or part of its functionality may be included in device 20 and/or device 30. The receiver 12 may take on other suitable configurations and may not include an antenna or antenna array. In one embodiment of the present invention, the receiver 12 may, for example, include an LCD display for displaying image data or other data, e.g. tracking data. In other embodiments, receiver 12 may be electrically connected, e.g. via wire or wireless (e.g., using the Bluetooth™ standard) connection, to a display unit, e.g. display unit 18 or workstation 14, to display data transmitted by in-vivo device 20 and/or processed by processing unit 17, 44, or workstation 14.

In one embodiment of the present invention, receiver 12 may, for example, receive and store data from imaging device 20, e.g. an image stream data captured and/or processed by processor 17 and later transfer the received data to a workstation 14, such as a personal computer, laptop or other portable or stationary computing devices, where the data may be further analyzed, stored, and/or displayed to a user, e.g. a health professional. Typically, workstation 14 may include processing unit 13, data processor storage unit 19, a disk drive, input-output devices, and display unit 18, e.g. a monitor, although alternate configurations are possible. Processing unit 13 may typically, as part of its functionality, act as a controller controlling the display of data for example, image data or other data. Display unit 18 may typically be a conventional video display, but may, in addition, be any other device capable of providing image or other data. Instructions or software for carrying out a method according to an embodiment of the invention may be included as part of workstation 14, for example stored in memory 19. In another embodiment, a processing unit such as processing unit 13 and/or a storage such as storage 49 may be included in device 20 and/or device 30.

In-vivo imaging systems suitable for use with embodiments of the present invention may be similar to various embodiments described, for example in U.S. Pat. No. 5,604,531, entitled "In-Vivo Video Camera System", assigned to the common assignee of the present application and incorporated herein by reference in its entirety, and/or U.S. patent application Ser. No. 09/800,470, filed Mar. 1, 2000 and/or U.S. Patent Application Publication Number 20010035902 published on Nov. 1, 2001 and entitled "Device and System for In-Vivo Imaging", also assigned to the common assignee of the present application and incorporated herein by reference in its entirety. For example, one or more of devices 20 and 30 may be similar to those described in U.S. Pat. No. 5,604,531, in application Ser. No. 09/800,470, or U.S. Patent Application Publication Number 20010035902. One or more of devices 20 and 30 may be capsule shaped, but other shapes may be used.

Other in-vivo systems, having other configurations, may be used. Of course, devices, systems, and structures, as described herein may have other configurations, sets of components, etc.

In some embodiments, after devices 20 and 30 are joined together one device, such as device 30, might pull or push the other device e.g. device 20, along, for example, as an engine might pull a train.

One of the devices, such as device 30 may for example be fitted with an instrument or set of tools or biopsy mechanism 32 to take a biopsy of endo-luminal tissue, cells or liquid and the other device, such as device 20, may for example have an imager 46 and control features to view or direct the biopsy procedure. Embodiments including a system which may include a plurality of in-vivo devices are described, for example, in Intentional Application number 2005/000510 entitled "METHOD, SYSTEM AND DEVICE FOR IN-VIVO. BIOPSY" filed on May 17, 2005 which is assigned to the assignee of the present invention and which is hereby incorporated by reference.

According to an embodiment of the invention either one or both devices 20 and 30 may include an arm or appendage such as for example an articulated arm as a biopsy mechanism. For example device 30 may be fitted with, an articulated arm 60 that may extend from the device 30 to grasp and collect a piece of tissue 72'. Examples of extendable arms or appendages that may be used with embodiments of the present invention are described in U.S. patent application Ser. No. 10/694,092 entitled "IN-VIVO EXTENDABLE ELEMENT DEVICE AND SYSTEM AND METHOD OF USE" to Iddan, and International Application Number 2003/01104 entitled "IMMOBILIZABLE IN VIVO SENSING DEVICE" to Gilad, each of which incorporated by reference herein in their entirety. Other arms or appendages and methods may be used.

According to some embodiments of the present invention, control of the devices of system 10 or various operations or functions may be enabled with RF or radio control. Alternatively or in addition, the application of a magnetic field may be used as a control of the device's functions. Similarly, ultrasound, microwave, or internal clock timed (e.g., pre-programmed) activations may be used as triggers to activate one or more functions of the system 10. Various functions may also be triggered in response to changes in environment such as pH, temperature or pressure.

According to an embodiment of the invention either one or more devices in system 10 may be equipped with, for example a small alarm or signal alert unit, such as unit 50 that may be activated when the two devices 20 and 30 are joined. The alert may be triggered by, for example, an increase in a magnetic field level e.g. produced by the connecting magnets 21 and 31, that would be expected upon the connection of the devices 20 and 30 and may assist in locating the devices. According to other embodiments of the present invention a transmitter, such as transmitter 41 may send a signal such as an RF signal to a data receiver and/or recorder when the two devices 20 and 30 are joined, possibly in response to a signal from an alarm unit such as unit 50.

In-vivo devices 30 and/or 20 are typically autonomous and may typically be self-contained. For example, device 20 and/or device 30 may be a capsule or another unit where all the components may be substantially contained within a container or shell, and where no wires or cables may be required to, for example, receive power or transmit information.

Figure 2A:
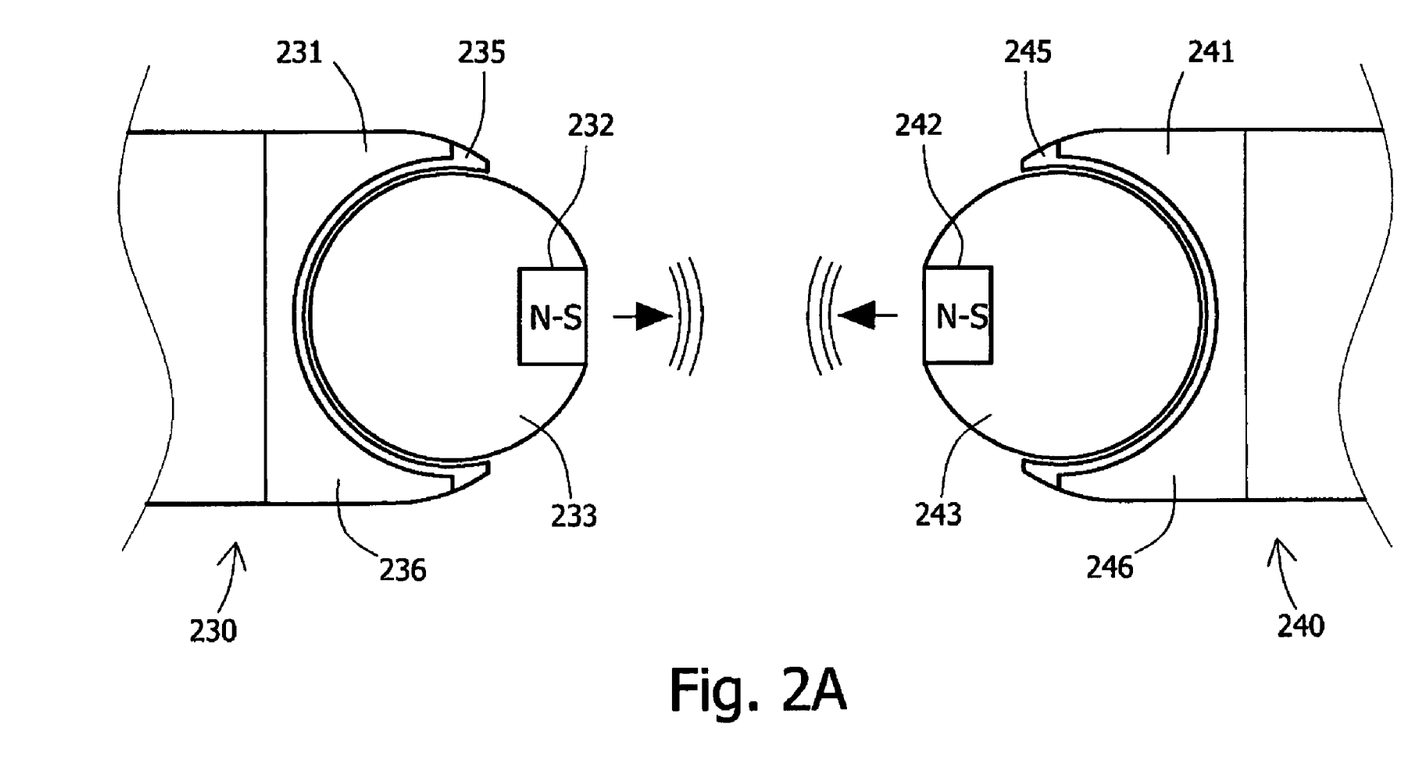
FIG. 2A is a schematic illustration of an in-vivo system in accordance with an embodiment of the present invention.

Reference is made to FIGS. 2A, which schematically illustrate two in-vivo devices which may include a connection unit, e.g. a ball-and-socket joint connection unit, for connecting the two in-vivo devices, in accordance with some embodiments of the present invention. According to one embodiment of the present invention, two ball-and-socket joint connection units such as units 235 and 245 may be positioned, respectively, at the edges of first and second in-vivo devices, such as an autonomous in-vivo devices 230 and 240. For example, the two ball-and-socket joint connection units may be connected on one side to the device's body or housing 231 and 241 and may be connected, on the other side, for example to two magnets 232 and 242. The two magnets 232 and 242, may produce a magnetic attraction force between the two joint balls, such that the devices 230 and 240 may be pulled towards one another.

Ball-and-socket joint connection units 235 and 245 may include joint balls 233 and 243 which may be seated in seats 238 and 248, and specifically in an annular or annular surface shaped bearing against the seats which is formed conically at one end of an essentially cylindrical joint casing 236 and 246. When used herein, terms like over, above, on, at, below, etc., are considered relative terms descriptive when a device is in a certain orientation relative to the viewer. Given a certain orientation, an optical system may be "below" or "to the side of" an image sensor.

According to some embodiments of the present invention, one of the joint balls 233 and 243 may be formed ferro magnetically while the other joint ball may be a magnet so that a magnetic attraction force is produced between the two joint balls 233 and 243 sitting in the joint socket 235 and 245 such that the devices 230 and 240 may be pulled towards one another.

Figure 2B:
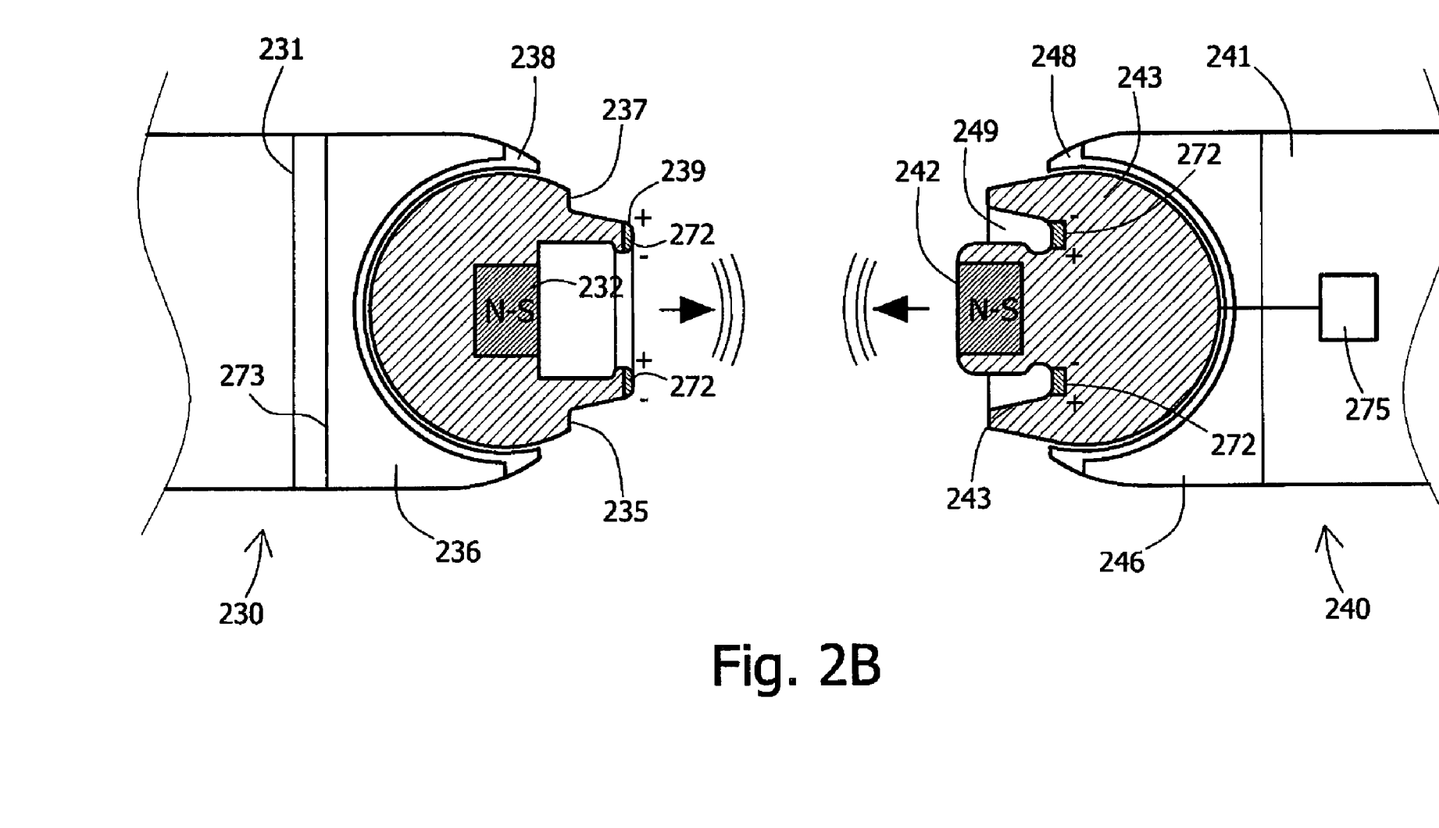
FIG. 2B is a schematic illustration of an in-vivo system in accordance with another embodiment of the present invention.

In one embodiment of the present invention, shown in FIG. 2B, an indentation 239 or other cavity, etc. may be provided or added to joint ball 233, while a protrusion 249 may be formed or added to joint ball 243, for example so that the devices 230 and 240 may securely be joined. For example, as the two devices are heading towards one another by the magnetic force which is produced by the two magnets 232 and 242, the joint ball 233 may be press fitted into the joint ball 243. E.g. protrusion 249 may be press fitted into indentation 239 such that the two devices are securely joined. Other suitable methods may be used for connecting device 230 to device 240.

According to some embodiments of the present invention one or more devices such as the devices 230 and 240, shown in FIG. 2B, may be electrically connected to each other. For example, the joint balls 233 and 243 may include one or more electric contact points, e.g. points 272, which may be located, for example at indentation 239 and protrusion 249. In some embodiments, devices 230 and 240 may include, for example an electric circuit 273 which may be connected to the electric contacts 272 and to one or more components of the devices 230 and 240, such as a power source and/or imager etc. In some embodiments, the contact points 272 may be electrically activated only when the devices 230 and 240 are joined, thus preventing an occurrence of a short circuit. For example, the electric circuit 273 may be kept turned off when the two devices 230 and 240 are disconnected and may be turned on during the connection of devices 230 and 240. According to some embodiments of the present invention the electric circuit 273 may be automatically activated, for example by a power switch 275, In some embodiments a power switch, such as power switch 275 may be activated by a magnetic power which may be created once the devices 230 and 240 are in close proximity e.g. when protrusion 249 is press fitted into indentation 239.

Figure 2C:
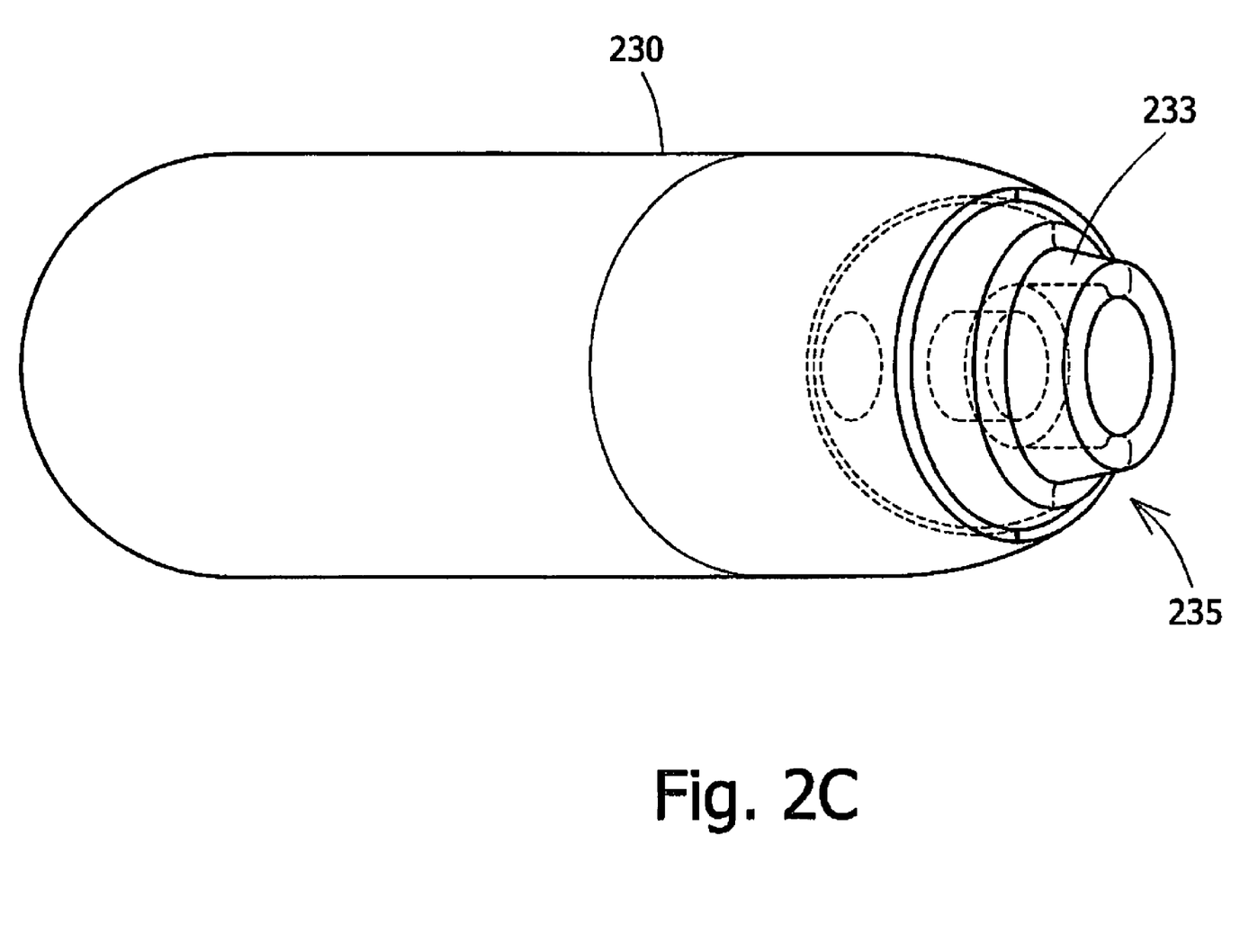
FIG. 2C is a schematic isometric view of an in-vivo device in accordance with an embodiment of the present invention.

Reference is now made to FIG. 2C showing an isometric view of an in-vivo device 230 which may include a connection unit, e.g. a ball-and-socket joint connection unit 235, in accordance with some embodiments of the present invention. The ball-and-socket joint connection unit 235 may include a joint ball 233 which may be hemispherically shaped at one side for permitting the rotation of the joint ball 233 in several axes, and ring shaped at the other side for connecting the joint ball 233 to other devices.

Figure 3:
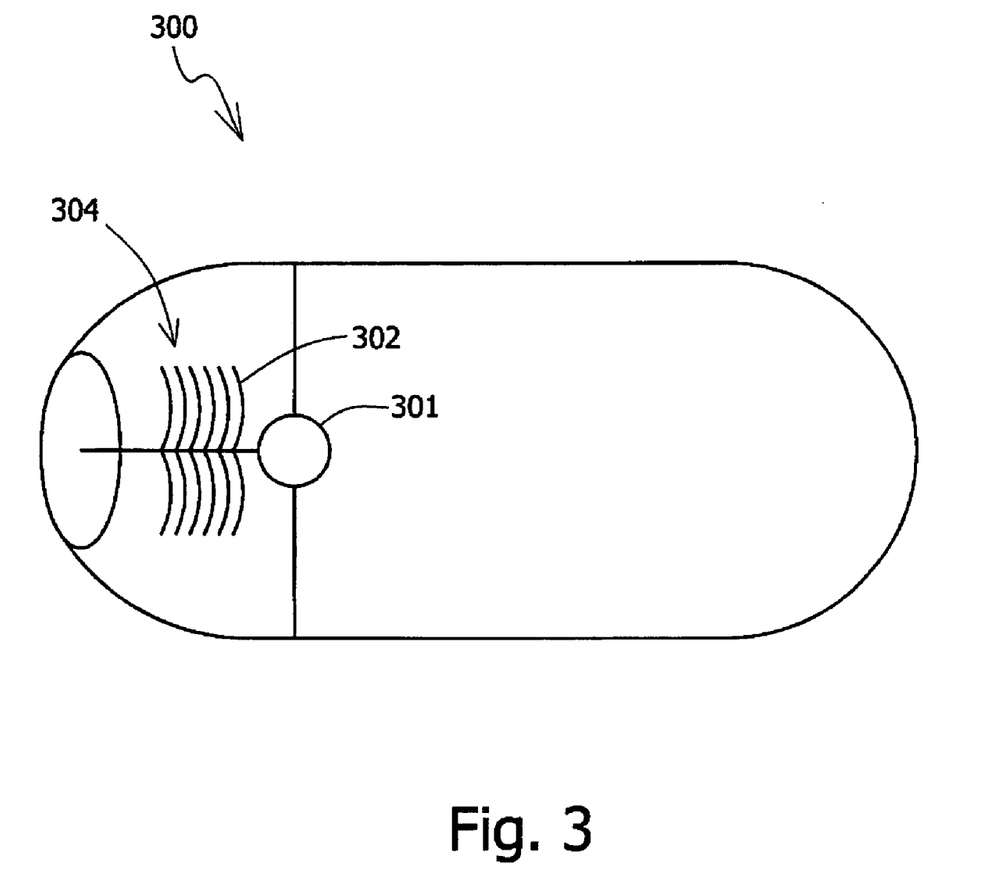
FIG. 3 is a schematic illustration of a device including a propulsion mechanism in accordance with an embodiment of the present invention.

Reference is made to FIG. 3, a schematic depiction of a device with a propulsion system, in accordance with an embodiment of the invention. Referring to FIG. 3, propulsion system generally referenced as 300 may be included in, for example, device 30 of FIG. 1A, but may be included in other suitable devices. The propulsion system may include for example a piston 301 which may move backwards and forwards against a membrane 304 inside the cylindrical portion of the device to generate suction. A series of valves 302 may be used to allow air or liquid to be pumped out of a cavity and to apply the resulting suction. An electromagnet that may be alternately turned on and off may supply the power for a pump that may generate suction. An electromagnetic squeeze box type pump may also be used to create suction. Such a squeezebox may also be used to provide propulsion for a device similar to the way that a jelly fish or squid squeezes liquid to provide thrust in a liquid environment For example, a membrane 304 or diaphragm that may be caused to vibrate within a liquid environment may push on or squeeze water from a container to provide thrust The container may have or be connected to a series of gill-like valves 302 that may permit intake of liquid to replace the liquid that had been expelled by the membrane. The valves 302 or gills may let water or liquid into the container slowly so as to not move the container backward as the liquid enters. The membrane 304 may be activated by for example a piston 301 or by electromagnetic force.

Figure 4:
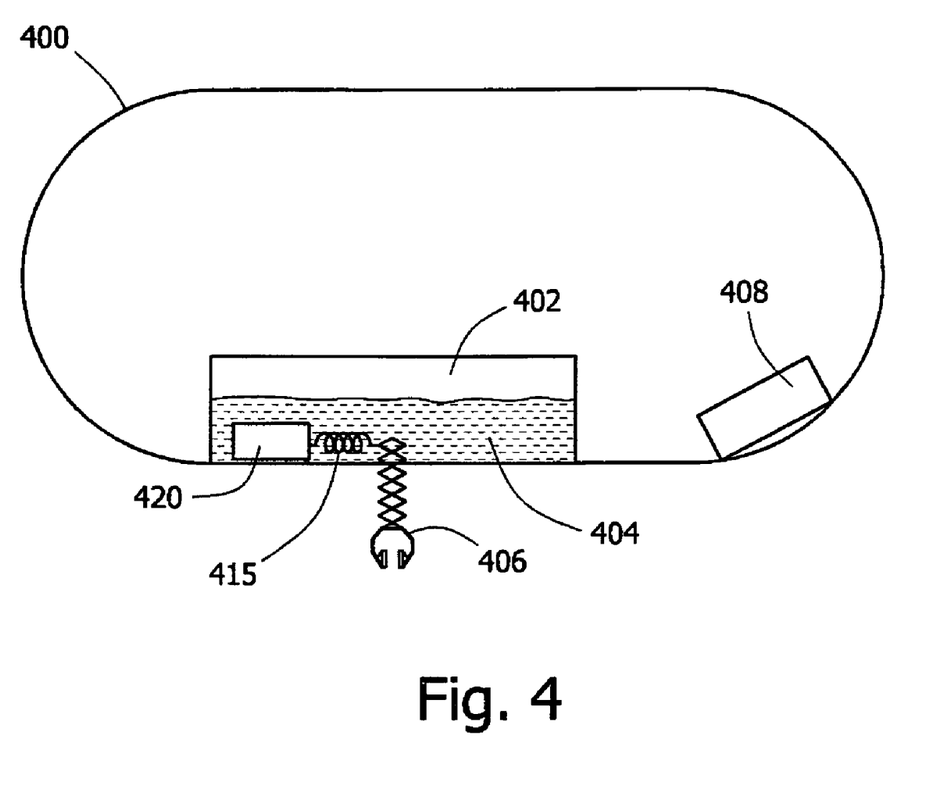
FIG. 4 is a schematic illustration of a device including an internal pushing mechanism in accordance with an embodiment of the present invention.

Reference is made to FIG. 4, a depiction of a device, such as an in-vivo device 400, with an internal pushing mechanism 410, in accordance with an embodiment of the invention. Referring to FIG. 4, internal pushing or moving mechanism 410 may be included in, for example device 30 of FIG. 1A, but may be included in other suitable devices. An internal pushing mechanism 410 may be used inside a device, such as device 410, to push collected samples into a receptacle 402 in the device 400 to free for example a set of forceps 406 to allow further biopsies to be taken and stored. The pushing mechanism 410 may include a spring 415 or other suitable element for freeing a sample from forceps 406 of the sample. The receptacle 402 that may store biopsy samples may contain for example formalin, alcohol or another suitable preservative 404 in which the samples may be stored until they are retrieved. The receptacle 402 of the device 400 which stores the samples may be easily removed after use of the device 400 for delivery to a laboratory.

The device 400 may be equipped with a small alarm 408 or sound alert device that may be activated when the device is released from the body. The alert may be triggered by, for example, an increase in ambient light that would be expected upon the release of the device from the body and may assist in locating the device upon such release. Control of the device or various operations or functions may be enabled with for example RF or radio controlled switching. Alternatively or in addition, the application of a magnetic field may be used as a control of the device's functions. Similarly, ultrasound, microwave, or internal clock timed (e.g., pre-programmed) activations may be used as triggers to activate one or more functions of the device. Various functions may also be triggered in response to changes in environment such as pH, temperature or press According to an embodiment of the invention either one or both devices 20 and 30, may have a specific gravity of about 1 or less, or a volume to weight ratio that enables the device to float, for example, in a body lumen liquid, for example the liquid typically found in the human stomach, or for example liquid that may be administered to a patent to fill a lumen such as the stomach.

Figure 5:
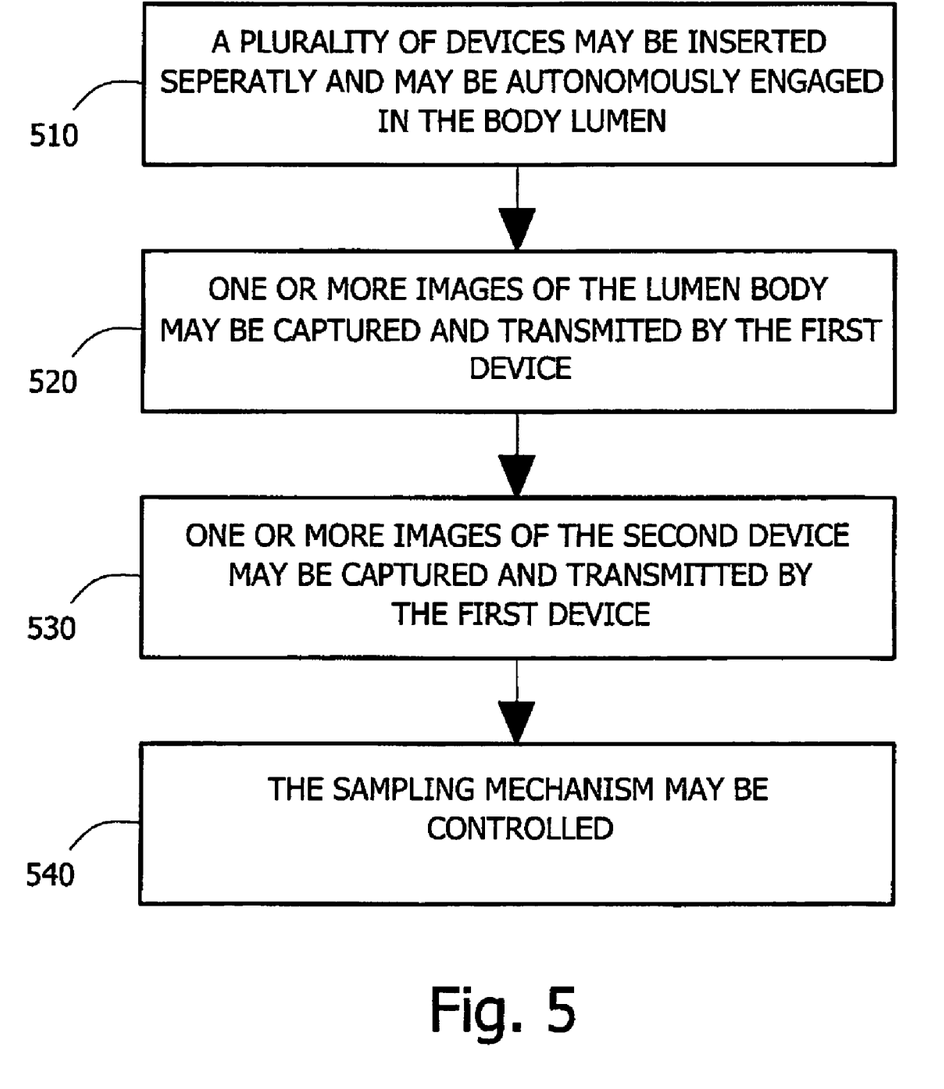
FIG. 5 is a schematic flow-chart of a method of imaging a body lumen and/or obtaining an in vivo sample, according to one embodiment of the present invention.

FIG. 5 is a schematic flow-chart of a method of imaging a body lumen and/or obtaining an in vivo sample, according to one embodiment of the present invention. In operation 510, a plurality of devices may be inserted separately e.g. one by one, into a body lumen, and may be autonomously engaged e.g. move from a separated configuration to a connected configuration by themselves, in the body lumen, for example by one or more magnets. In some embodiments a first device may include an imager and a transmitter for transmitting image data, and a second device may include, for example a sampling mechanism. In operation 520, one or more images of the lumen body may be captured and transmitted by the first device. In operation 530, one or more images of for example the second device or at least a portion of the second device may be captured and transmitted by the first device. In operation 540, the sampling mechanism may be controlled e.g., to obtain a biopsy sample from within the body lumen.

It will be appreciated by persons skilled in the art that the present invention is not limited to what has been particularly shown and described hereinabove. Alternate embodiments are contemplated which fall within the scope of the invention.

What is claimed is:

1. An in-vivo system comprising:
a plurality of unconnected in-vivo devices,
wherein a first in-vivo device comprises an imager and a transmitter,
wherein each of the devices may be detachably coupled to another of the devices by a magnetic connection, and
wherein an in-vivo device of the in-vivo devices comprises a ball-and-socket joint connecting unit.

2. The system according to claim 1, wherein
a second in-vivo device of the devices comprises a sampling mechanism.

3. The device according to claim 2 wherein said first in-vivo device further comprises an illumination source.

4. The device according to claim 2 wherein said first in-vivo device further comprises an alert unit.

5. The device according to claim 2 wherein one device of said devices further comprises a processor.

6. The system according to claim 1, wherein said imager is configured to image at least a portion of a second device of the devices.

7. The system according to claim 1, wherein said joint ball comprises a magnet.

8. The system according to claim 1, wherein said joint ball comprises a ferro magnet.

9. The system according to claim 1, wherein a first in-vivo device of the devices comprises:
- a magnet; and
- a second in-vivo device of the devices comprises a ferro magnet.

10. The system according to claim 1, wherein said devices are autonomous swallowable capsules.

11. The system according to claim 1, wherein said devices are floatable.

12. The system according to claim 1, comprising a storage unit.

13. The device according to claim 1 wherein one device of said devices further comprises a propulsion system.

14. The system according to claim 1, wherein said connecting unit further comprises an electrical connection unit.

15. The system according to claim 14, wherein said electrical connection unit is not activated unless said in vivo device is coupled to another in vivo device.

16. The system according to claim 1, wherein said joint ball comprises an electrical connection unit.

17. The system according to claim 1,
wherein said first device and a second device each comprise a respective ball-and-socket connection unit, and
wherein said joint ball of a first device comprises a protrusion, and said joint ball of a second device comprises an indentation configured for securely receiving said protrusion.

18. An in-vivo system comprising:
a plurality of in-vivo devices, wherein each of the devices is connected to another of the devices by a magnetic connection, wherein a first of the in-vivo devices comprises an imager and a transmitter, and wherein at least one of the in-vivo devices comprises a ball-and-socket joint connecting unit.

19. The system according to claim 18, wherein said joint ball comprises a magnet.

20. The system according to claim 18, wherein said joint ball comprises a ferro magnet.

* * * * *

UNITED STATES PATENT AND TRADEMARK OFFICE
CERTIFICATE OF CORRECTION

PATENT NO.        : 7,678,043 B2
APPLICATION NO.   : 11/319772
DATED             : March 16, 2010
INVENTOR(S)       : Zvika Gilad Page 1 of 1

It is certified that error appears in the above-identified patent and that said Letters Patent is hereby corrected as shown below:

Column 8, line 62 (Claim 3, line 1) "device" should be replaced with -- system --.

Column 8, line 64 (Claim 4, line 1) "device" should be replaced with -- system --.

Column 8, line 66 (Claim 5, line 1) "device" should be replaced with -- system --.

Column 9, line 21 (Claim 13, line 1) "device" should be replaced with -- system --.

Signed and Sealed this
Fifteenth Day of March, 2011

David J. Kappos
*Director of the United States Patent and Trademark Office*